US012497426B2

(12) United States Patent
Lu et al.

(10) Patent No.: US 12,497,426 B2
(45) Date of Patent: Dec. 16, 2025

(54) RHAMNOLIPID OLIGO-ESTERS

(71) Applicant: Evonik Operations GmbH, Essen (DE)

(72) Inventors: Xin Lu, Essen (DE); Jochen Kleinen, Heinsberg (DE); Hans Henning Wenk, Muelheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 353 days.

(21) Appl. No.: 18/005,942

(22) PCT Filed: Jul. 12, 2021

(86) PCT No.: PCT/EP2021/069280
§ 371 (c)(1),
(2) Date: Jan. 18, 2023

(87) PCT Pub. No.: WO2022/017844
PCT Pub. Date: Jan. 27, 2022

(65) Prior Publication Data
US 2023/0348514 A1 Nov. 2, 2023

(30) Foreign Application Priority Data
Jul. 22, 2020 (EP) .................................... 20187101

(51) Int. Cl.
*C07H 15/06* (2006.01)
*A61K 8/60* (2006.01)
*A61Q 15/00* (2006.01)
*C07H 1/00* (2006.01)

(52) U.S. Cl.
CPC ............. *C07H 15/06* (2013.01); *A61K 8/604* (2013.01); *A61Q 15/00* (2013.01); *C07H 1/00* (2013.01)

(58) Field of Classification Search
CPC .......... C07H 15/06; C07H 1/00; A61K 8/604; A61Q 15/00
See application file for complete search history.

(56) References Cited

U.S. PATENT DOCUMENTS

| | | | |
|---|---|---|---|
| 8,466,248 | B2 | 6/2013 | Meyer et al. |
| 8,911,982 | B2 | 12/2014 | Schaffer et al. |
| 9,005,928 | B2 | 4/2015 | Schaffer et al. |
| 9,068,211 | B2 | 6/2015 | Schaffer et al. |
| 9,085,787 | B2 | 7/2015 | Schaffer et al. |
| 9,102,968 | B2 | 8/2015 | Schaffer et al. |
| 9,157,108 | B2 | 10/2015 | Schaffer et al. |
| 9,243,212 | B2 | 1/2016 | Kuppert et al. |
| 9,271,908 | B2 | 3/2016 | Allef et al. |
| 9,351,485 | B2 | 5/2016 | Giessler-Blank et al. |
| 9,434,755 | B2 | 9/2016 | Schilling et al. |
| 9,580,720 | B2 | 2/2017 | Schaffer et al. |
| 10,174,353 | B2 | 1/2019 | Thum et al. |
| 10,292,924 | B2 | 5/2019 | Schilling et al. |
| 10,544,384 | B2 | 1/2020 | Scheuermann et al. |
| 10,604,722 | B2 | 3/2020 | Schilling et al. |
| 10,676,495 | B2 | 6/2020 | Lu et al. |
| 10,941,173 | B2 | 3/2021 | Lu et al. |
| 10,988,713 | B2 | 4/2021 | Schilling et al. |
| 11,236,372 | B2 | 2/2022 | Wessel et al. |
| 11,254,896 | B2 | 2/2022 | Kuppert et al. |
| 11,464,717 | B2 | 10/2022 | Wenk et al. |
| 11,591,547 | B2 | 2/2023 | Xue et al. |
| 11,606,963 | B2 | 3/2023 | Schilling et al. |
| 2012/0220464 | A1 | 8/2012 | Giessler-Blank et al. |
| 2013/0035403 | A1 | 2/2013 | Schaffer et al. |
| 2013/0130319 | A1 | 5/2013 | Schaffer et al. |
| 2014/0148588 | A1 | 5/2014 | Schilling et al. |
| 2014/0296125 | A1 | 10/2014 | Kuppert et al. |
| 2014/0296168 | A1 | 10/2014 | Schilling et al. |
| 2014/0349902 | A1 | 11/2014 | Allef et al. |
| 2015/0056658 | A1 | 2/2015 | Schaffer et al. |
| 2015/0056659 | A1 | 2/2015 | Schaffer et al. |
| 2015/0056660 | A1 | 2/2015 | Schaffer et al. |
| 2015/0056661 | A1 | 2/2015 | Schaffer et al. |
| 2015/0247151 | A1 | 9/2015 | Schaffer et al. |
| 2016/0045424 | A1 | 2/2016 | Schwab et al. |
| 2016/0249604 | A1 | 9/2016 | Giessler-Blank et al. |
| 2017/0094968 | A1 | 4/2017 | Sieverding |
| 2017/0096695 | A1 | 4/2017 | Thum et al. |
| 2017/0306264 | A1 | 10/2017 | Peggau et al. |
| 2017/0335238 | A1 | 11/2017 | Schilling et al. |
| 2018/0016525 | A1 | 1/2018 | Scheuermann et al. |

(Continued)

FOREIGN PATENT DOCUMENTS

| | | |
|---|---|---|
| DE | 10 2008 001 788 | 11/2009 |
| DE | 10 2012 201 360 | 8/2013 |

(Continued)

OTHER PUBLICATIONS

International Search Report dated Sep. 24, 2021, in PCT/EP2021/069280, 7 pages.
Written Opinion dated Sep. 24, 2021, in PCT/EP2021/069280, 9 pages.
Extended European Search Report dated May 3, 2021, in European Patent Application No. 20187101.9, 12 pages.
U.S. Appl. No. 15/151,021, filed May 10, 2016, Giessler-Blank et al.
U.S. Appl. No. 15/311,217, filed Nov. 15, 2016, Ewald Sieverding.
U.S. Appl. No. 15/509,685, filed Mar. 8, 2017, Peggau et al.
U.S. Appl. No. 14/783,142, filed Oct. 8, 2015, Schwab et al.
U.S. Appl. No. 16/333,719, filed Mar. 15, 2019, Thum et al.

(Continued)

*Primary Examiner* — Michael P Cohen
(74) *Attorney, Agent, or Firm* — Grüneberg and Myers PLLC

(57) ABSTRACT

A rhamnolipid ester is useful as a cosmetic additive. A method of its production involves providing at least one rhamnolipid, reacting the at least one rhamnolipid with at least one coupling reagent, reacting the at least one rhamnolipid with a polyhydric alcohol having 1 to 32 carbon atoms, and optionally purifying the at least one rhamnolipid ester.

19 Claims, No Drawings

(56) References Cited

U.S. PATENT DOCUMENTS

| | | | | |
|---|---|---|---|---|
| 2018/0023040 | A1 | 1/2018 | Schilling et al. | |
| 2019/0031977 | A1 | 1/2019 | Kuppert et al. | |
| 2019/0040095 | A1 | 2/2019 | Lu et al. | |
| 2019/0233856 | A1 | 8/2019 | Thum et al. | |
| 2019/0256542 | A1* | 8/2019 | Lu | C07H 1/00 |
| 2019/0269158 | A1 | 9/2019 | Schilling et al. | |
| 2019/0271020 | A1 | 9/2019 | Thum et al. | |
| 2019/0307657 | A1 | 10/2019 | Wenk et al. | |
| 2020/0199492 | A1 | 6/2020 | Xue et al. | |
| 2020/0214959 | A1 | 7/2020 | Lu et al. | |
| 2020/0407761 | A1 | 12/2020 | Wessel et al. | |
| 2021/0337835 | A1 | 11/2021 | Schilling et al. | |
| 2021/0371773 | A1 | 12/2021 | Brandt et al. | |
| 2022/0183958 | A1 | 6/2022 | Kleinen et al. | |
| 2022/0186048 | A1 | 6/2022 | Reuter et al. | |
| 2022/0186075 | A1 | 6/2022 | Reuter et al. | |

FOREIGN PATENT DOCUMENTS

| | | | | |
|---|---|---|---|---|
| EP | 1 889 623 | A2 | 2/2008 | |
| EP | 1 889 623 | A3 | 4/2009 | |
| EP | 2 735 605 | | 5/2014 | |
| EP | 2 786 742 | | 10/2014 | |
| EP | 3419985 | | 1/2019 | |
| EP | 4 155 371 | | 3/2023 | |
| WO | 01/10447 | | 2/2001 | |
| WO | 2008/013899 | | 1/2008 | |
| WO | 2012/013554 | | 2/2012 | |
| WO | 2016/131801 | | 8/2016 | |
| WO | 2017/144317 | | 8/2017 | |
| WO | WO-2017144317 | A1 * | 8/2017 | A61K 8/604 |
| WO | 2018/195613 | | 11/2018 | |
| WO | 2019/038125 | | 2/2019 | |
| WO | 2021/180612 | | 9/2021 | |
| WO | 2021/190993 | | 9/2021 | |
| WO | 2022/233700 | | 11/2022 | |

OTHER PUBLICATIONS

U.S. Appl. No. 16/334,781, filed Mar. 20, 2019, Thum et al.
U.S. Appl. No. 17/369,275, filed Jul. 7, 2021, Schilling et al.
U.S. Appl. No. 16/631,248, filed Jan. 15, 2020, Lu et al.
U.S. Appl. No. 17/436,104, filed Sep. 3, 2021, Kleinen et al.
U.S. Appl. No. 16/963,277, filed Jul. 20, 2020, Brandt et al.
U.S. Appl. No. 17/643,630, filed Dec. 10, 2021, Reuter et al.
U.S. Appl. No. 17/547,575, filed Dec. 10, 2021, Reuter et al.
Nurfarahin, et al., "Development of Palm Fatty Acid Distillate-Containing Medium for Biosurfactant Production by *Pseudomonas* sp. LM19", Molecules, 2019, vol. 24, pp. 1-21.
Zgola-Grzeskowiak, et al., "Isolation, preconcentration and determination of rhamnolipids in aqueous samples by dispersive liquid-liquid microextraction and liquid chromatography with tandem mass spectrometry", Talanta, 2011, vol. 83, pp. 744-750.

* cited by examiner

RHAMNOLIPID OLIGO-ESTERS

CROSS-REFERENCE TO RELATED APPLICATIONS

This application is the National Stage entry under § 371 of International Application No. PCT/EP2021/069280, filed on Jul. 12, 2021, and which claims the benefit of priority to European Application No. 20187101.9, filed on Jul. 22, 2020. The content of each of these applications is hereby incorporated by reference in its entirety.

BACKGROUND OF THE INVENTION

Field of the Invention

The invention relates to new rhamnolipid esters, to a method of their production and also to the use of the rhamnolipid ester as cosmetic additives.

Description of Related Art

EP3419985 discloses rhamnolipid esters of rhamnolipids with aliphatic alcohols having 7 to 32 carbon atoms WO2019038125 discloses a dispersion, in particular an emulsion, containing at least one rhamnolipid derivative and also to the use of the rhamnolipid derivatives as emulsifier or dispersing aid, wherein the rhamnolipid derivatives are certain rhamnolipid esters or rhamnolipid amides. Miao et al., Journal of Surfactants and Detergents, 17 (6), 2014; 1069-1080, describes the synthesis of di-rhamnolipid ethyl esters by esterification with ethanol and also the suitability of the esters as nonionic surfactant.

WO2001010447 and EP1889623 disclose the pharmaceutical and cosmetic applications of rhamnolipids and short-chain rhamnolipid esters (C1-C6; methyl to hexyl esters, linear or branched), in particular in wound healing.

WO2018195613 discloses a deodorant composition for controlling body odor of localized areas of the body, such as the underarm, or textiles, wherein the composition comprises specific components in particular amounts combined with rhamnolipids for acting specifically on *Corynebacterium xerosis*.

WO2008013899 discloses an application for a cleaning formulation comprising 0.01% to 99.9% of rhamnolipid; and the balance being a carrier.

SUMMARY OF THE INVENTION

It is an object of the invention to provide new anti-perspirant substances, which are also suited to suppress body odor.

Surprisingly, it has been found that the rhamnolipid esters described below are able to achieve the set object of the invention.

The present invention therefore provides rhamnolipid esters as described below.

The invention further provides a process for the preparation of the rhamnolipid esters according to the invention, and the use thereof.

One advantage of the present invention is that the rhamnolipid esters of the instant invention have excellent properties in the reduction of malodors and control sweating Another advantage of the present invention is that the rhamnolipid esters of the instant invention can be added to numerous formulation without giving instabilities.

A further advantage of the present invention is that the rhamnolipid esters according to the invention increase the mildness of formulations.

A yet further advantage of the present invention is that a process for the preparation of the rhamnolipid esters according to the invention can be performed at industrial scale on standard assets.

A further advantage of the present invention is that the compositions according to the invention potentially decrease the release of zinc and aluminium into the environment, as the rhamnolipid esters of the instant invention are an excellent alternative.

A yet further advantage is that the preparation process is after application of the rhamnolipid esters of the instant invention, the skin becomes less defatted and skin hydration is improved.

A further advantage is that the product can be isolated and worked up in an excellent manner.

A yet further advantage is that the rhamnolipid esters according to the invention do not cause unwanted skin irritation, while leaving a good smooth, silky-soft skin feel.

The terms “rhamnolipid” and “rhamnolipid ester” in connection with the present invention also always include their corresponding salts.

The terms “rhamnolipid radical” in connection with the present invention is understood as that part of the general formula (I) shown below, that is within the z-indexed bracket.

The term “di-rhamnolipid” in connection with the present invention is understood as meaning compounds of the general formula (I) shown below, where A=H and z=1 or salts thereof, in which n=1.

The term “mono-rhamnolipid” in connection with the present invention is understood as meaning compounds of the general formula (I) shown below, where A=H and z=1 or salts thereof, in which n=0.

Distinct rhamnolipids are abbreviated according to the following nomenclature:

- “diRL-CXCY” is understood as meaning di-rhamnolipids of the general formula (I), where A=H and z=1 or salts thereof, in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.
- “monoRL-CXCY” is understood as meaning mono-rhamnolipids of the general formula (I), where A=H and z=1 or salts thereof, in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used therefore does not distinguish between “CXCY” and “CYCX”.

For rhamnolipids where m=0, monoRL-CX or diRL-CX is used accordingly.

If one of the abovementioned indices X and/or Y is provided with “:N”, this signifies that the respective radical $R^1$ and/or $R^2$=an unbranched, unsubstituted hydrocarbon radical having X-3 or Y-3 carbon atoms having N double bonds.

Analogous nomenclature is used for rhamnolipid esters in the form di/monoRL-CXCY:N esters.

The “pH” in connection with the present invention is defined as the value which is measured for the corresponding substance at 25° C. after stirring for 5 minutes using a pH electrode calibrated in accordance with ISO 4319 (1977).

Unless stated otherwise, all percentages (%) given are percentages by mass.

The present invention provides rhamnolipid ester of the general formula (I)

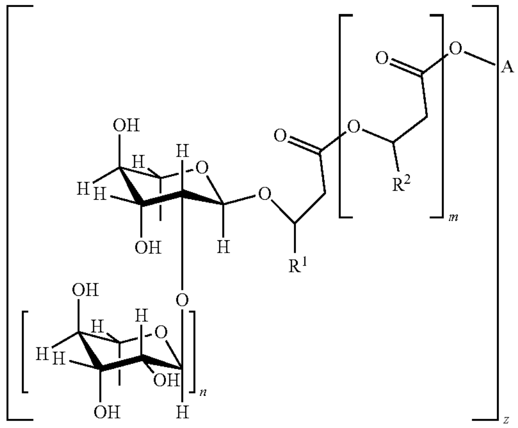

general formula (I), where m=independently of one another, identical or different, 2, 1 or 0, in particular 1 or 0, n=independently of one another, identical or different, 1 or 0, in particular 1, z=2 to 10, in particular 2 to 4, most preferably 2, $R^1$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, $R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, and A is a z-valent organic radical.

DETAILED DESCRIPTION OF THE INVENTION

Preferred rhamnolipid esters according to the instant invention are those, where the rhamnolipid radical is selected from the radicals of diRL-C10C10, diRL-C8C10, diRL-C10C12, diRL-C10C12:1 and monoRL-C10C10.

Particularly preferred rhamnolipid esters according to the instant invention are characterized in that z=2 and A is selected from the group of two valent hydrocarbyl radicals, which can be substituted by one or more hydroxyl group, preferably selected from the group consisting of

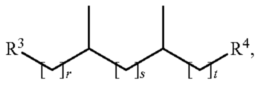

where $R^3$ and $R^4$ are selected from $CH_3$ and H, r=0 to 3, s=0 to 24, and t=0 to 24, wherein the structures with $R^3$=$R^4$=H, r=t=0, s=0 to 24, preferably 1 to 14, $R^3$=H, $R^4$=$CH_3$, r=0, s=0 to 2, t=0 to 23, preferably 1 to 15, $R^3$=$CH_3$, $R^4$=$CH_3$, r=0 to 3, s=0 to 2, t=0 to 23, preferably 1 to 15, are more preferred, with the structures with $R^3$=$R^4$=H, r=t=0, s=0 to 8, 10, 12 or 14, $R^3$=H, $R^4$=$CH_3$, r=0, s=0 or 1, t=0, $R^3$=H, $R^4$=$CH_3$, r=0, s=0, t=3, 7, 9, 11 or 13, $R^3$=$CH_3$, $R^4$=$CH_3$, r=s=2, t=0, are most preferred.

Other particularly preferred rhamnolipid esters according to the instant invention with z=2 and A is selected from the group of two valent hydrocarbyl radicals, which can be substituted by one or more hydroxyl group, have A selected from

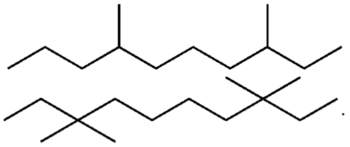

Alternatively particularly preferred rhamnolipid esters according to the instant invention are characterized in that z=2 and A is selected from the group of

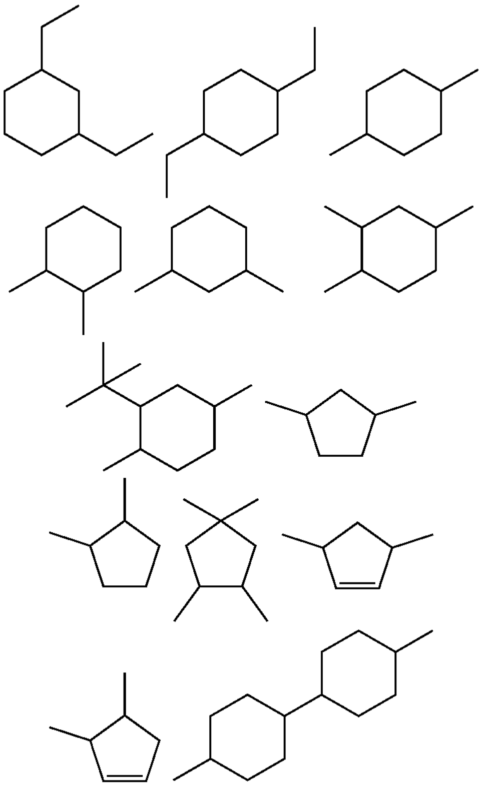

-continued

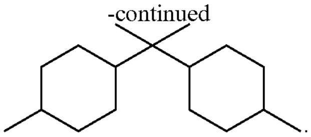

Further alternatively particularly preferred rhamnolipid esters according to the instant invention are characterized in that z=2 and A is selected from the group of

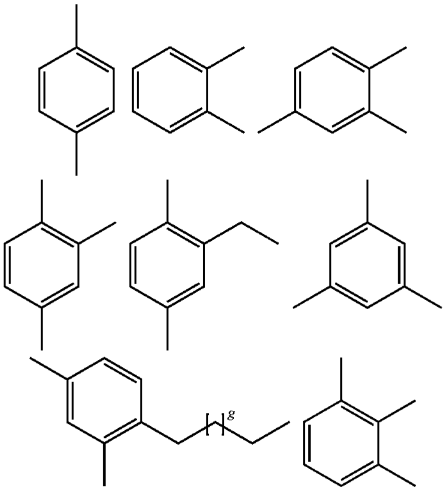

g = 0 bis 10

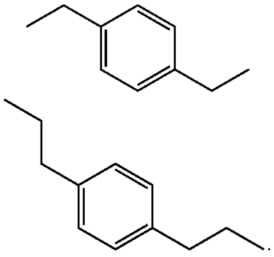

Particularly preferred rhamnolipid esters according to the instant invention are characterized in that z=2, the rhamnolipid radical is selected from the radicals of diRL-C10C10, diRL-C8C10, diRL-C10C12, diRL-C10C12:1 and monoRL-C10C10, and and A is selected from the group of

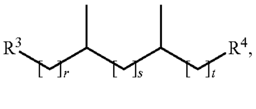

where $R^3=R^4=H$, r=t=0, s=0 to 8, 10, 12 or 14,

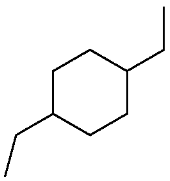

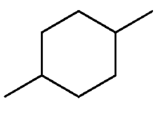

-continued

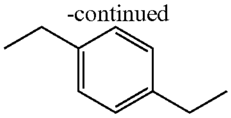

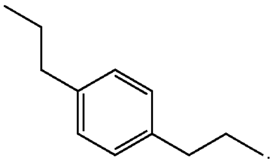

Particularly preferred according to the instant invention the rhamnolipid esters constitute a mixture composition of different rhamnolipid ester of the general formula (I).

The rhamnolipid esters according to the invention are preferably mixture compositions of rhamnolipid esters which are characterized in particular in that they contain mono- and di-rhamnolipid esters and/or mixed mono-/di-rhamnolipid esters, the latter being characterized by at least one mono-rhamnolipid-radical and at least one di-rhamnolipid-radical in one molecule.

Depending on the application, it may be preferred that in the mixture compositions according to the invention there are more percent by weight of mono-rhamnolipid-radicals than di-rhamnolipid radicals or more percent by weight of di-rhamnolipid-radicals than mono-rhamnolipid-radicals, where the percentages by weight refer to all of the mono- and di-rhamnolipid-radicals present in the rhamnolipid-ester.

Thus, for example, the rhamnolipid-ester as mixture composition according to the invention can comprise, for example, more than 60% by weight, in particular more than 80% by weight, or even more than 95% by weight, of di-rhamnolipid radicals, or else also for example more than 60% by weight, in particular more than 80% by weight, or even more than 95% by weight, of mono-rhamnolipid radicals, where the percentages by weight refer to all of the mono- and di-rhamnolipid radicals present in the rhamnolipid-ester.

The present invention further provides a process for the preparation of rhamnolipid esters comprising the process steps A) provision of at least one rhamnolipid, B) reaction of the rhamnolipid with at least one coupling reagent, C) reaction of the rhamnolipid activated by process step B) with a polyhydric alcohol having 1 to 32 carbon atoms, and optionally D) purification of the rhamnolipid ester.

Process step A) is carried out according to the generally known processes of the prior art, in particular using genetically modified microorganisms which preferably overexpress rhamnolipid synthesis genes, these genes preferably being selected from rhlA, rhlB and rhlC. Corresponding instructions can be found by the person skilled in the art in e.g. US2014296168 and WO2012013554.

It is preferred according to the invention that in process step B) the coupling reagent used is at least one selected from the group comprising, preferably consisting of, dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl)carbodiimide metho-p-toluenesulphonate, N-benzyl-N'-3' dimethylaminopropyl-carbodiimide hydrochloride, 1-ethyl-3-(3-dimethylamino-propyl)carbodiimide, N-ethylcarbodiimide hydrochloride and carbonyldiimidazole, particularly preferably dicyclohexylcarbodiimide and diisopropylcarbodiimide.

Likewise, it is preferred according to the invention that in process step C) at least one catalyst selected from the group comprising, preferably consisting of, N-ethyldiisopropylamine, trialkylamines, pyridine, 4-dimethylaminopyridine and hydroxybenzotriazole, in particular hydroxybenzotriazole, is used.

Processes preferred according to the invention preferably lead to the rhamnolipid esters which are described as preferred rhamnolipid esters according to the invention above.

Thus, for example, preferably in process step A) preferably rhamnolipids selected from diRLC10C10, diC8C10, diRLC10C12, diRLC10C12:1 and monoRLC10C10 or mixtures thereof are used.

Accordingly the use of alcohols in process step C) is preferred selected from the group of 1,2-ethanediol, 1,2-propanediol, 1,3-propanediol, 1,4-butanediol, 1,3-butanediol, 1,5-pentanediol, 1,2-hexanediol, 2,5-hexanediol, 1,6-hexanediol, 1,7-heptanediol, 1,8-octandiol, 2,6-dimethyloctane-1,8-diol, 1,9-nonanediol, 1,10-decanediol, 1,2-decanediol, 2,2,9,9-tetramethyl-1,10-decanediol, 1,12-dodecanediol, 1,2-dodecanediol, 1,2-tetradecanediol, 1,14-tetradecanediol, 1,16-hexadecanediol and 1,2-hexadecanediol.

The use of alcohols in process step C) selected from the group 1,4-cyclohexanediol, 1,2-cyclohexanediol, 1,3-cyclohexanediol, 1,2-cyclopentanediol, 1,3-cyclopentanediol, 4,4-dimethyl-1,2-cyclopentanediol, 4-cyclopentene-1,3-diol, 3-cyclopentene-1,2-diol, 2-tea-butyl-1,4-cyclohexanediol, 2-methyl-1,4-cyclohexanediol, 1,3-cyclohexanedimethanol, 1,4-cyclohexanedimethanol, 4,4'-isopropylidenedicyclohexanol and 4,4'-bicyclohexanol, is alternatively preferred.

The use of alcohols in process step C) selected from the group 1,4-benzenediol, methylhydroquinone, 1,2-benzenediol, 1,3-benzenediol, 1,3-dihydroxy-4-methylbenzene, 4-methyl-1,2-benzenediol, 3,5-dihydroxytoluene, 2,6-dihydroxytoluene, 4-butyl-1,3-benzenediol, 4-hexylresorcinol, 1,4-benzenedimethanol and 1,4-bis(2-hydroxyethyl)benzene is alternatively preferred.

The use of alcohols in process step C) selected from the group 1,2-ethanediol, 1,3-propanediol, 1,4-butanediol, 1,5-pentanediol and 1,6-hexanediol, 1,8-octandiol, 1,10-decanediol, 1,12-dodecanediol, 1,4-cyclohexanedimethanol, 1,4-Cyclohexanediol, 1,4-benzenedimethanol and 1,4-bis(2-hydroxyethyl)benzene is very much preferred.

The invention further provides the rhamnolipid esters obtainable by the process according to the invention, The rhamnolipid esters according to the invention can advantageously be incorporated into in particular cosmetic formulations, preferably for anti-perspirant applications.

Consequently, the present invention further provides the use of the rhamnolipid esters according to the invention for producing formulations, in particular cosmetic formulations, and the formulations themselves, in particular cosmetic formulations, preferably for anti-perspirant applications, which comprise the rhamnolipid esters according to the invention.

The formulations according to the invention are preferably aqueous formulations.

The term "aqueous formulation" in connection with the present invention is to be understood as meaning a formulation which comprises at least 5% by weight of water, based on the overall composition under consideration.

According to the invention, it is preferred if the formulations according to the invention comprise the rhamnolipid esters according to the invention in an amount of from 0.05% by weight to 40% by weight, preferably from 0.1% by weight to 20% by weight, particularly preferably from 0.2% by weight to 5% by weight, where the percentages by weight refer to the total formulation.

Preferred formulations according to the invention comprise, in addition to the rhamnolipid esters according to the invention, at least one further additional component.

The formulations according to the invention can further comprise at least one additional component selected from the group of emollients,
emulsifiers,
thickeners/viscosity regulators/stabilizers,
UV light protection filters,
antioxidants,
hydrotropes (or polyols),
solids and fillers,
film formers,
pearlescence additives,
deodorant and antiperspirant active ingredients,
insect repellents,
self-tanning agents,
surfactants,
perfumes,
preservatives,
propellants,
conditioners,
dyes,
cosmetic active ingredients,
care additives,
superfatting agents,
solvents,
wherein perfumes, antiperspirant active ingredients and propellants are preferably comprised.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts used of these components, reference is made expressly to the relevant handbooks known to the person skilled in the art, for example K. Schrader, "Grundlagen and Rezepturen der Kosmetika [Fundamentals and principles of cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The rhamnolipid esters according to the invention and the formulations according to the invention comprising the rhamnolipid esters according to the invention can be used advantageously for inhibiting body odor.

The present invention further provides the cosmetic use of the rhamnolipid esters according to the invention and/or of the formulations according to the invention in anti-perspirant applications.

The present invention further provides the cosmetic use of the rhamnolipid esters according to the invention and/or of the formulations according to the invention for inhibiting sweat.

The examples listed below describe the present invention by way of example, without any intention of restricting the invention, the scope of application of which is apparent from the entirety of the description, to the embodiments specified in the examples.

EXAMPLES

Example 1: Preparation of Di-Rhamnolipids

A fermentation with a recombinant strain *Pseudomonas putida* KT2440S pBBR[1]MCS2-Plac-rhlABC-T-Ptac-rhlC-T was carried out. The construction of the strain was described in US2014296168. The preculture in the shake flask was carried out as described in WO2012013554. For the main culture, a mineral medium (M9) was likewise used. The fermentation takes place in a glucose-limited fed-batch process in a 2 litre fermenter. The feeding in of glucose was regulated by reference to the dissolved-oxygen signal. The oxygen partial pressure of the fermentation broth was regulated at 20% saturation via the stirrer speed. The pH was regulated to 7 via a pH electrode and addition of 2M sulphuric acid or of a 20% by weight ammonia solution. In order to prevent excessive foaming of the fermentation broth, the antifoam DOW Corning 1500 was metered in as required. The fermentation was conducted over 4 days to a dry biomass of 15 Wl. The rhamnolipid concentration was determined by HPLC and was 9.8 g/l. After separating off the cells by means of centrifugation at 10 000 g, the fermentation broth was adjusted to a pH of 3.1 by adding concentrated $H_2SO_4$. Renewed centrifugation gave a pasty solid concentrate with an RL fraction of 45% by weight and with a viscosity of >10 000 mPas. With continuous stirring, a 50% strength by weight aqueous KOH solution was added to the pasty suspension of the concentrated rhamnolipid precipitate and a pH of 6 was established. The pasty mass liquefied at this point with an accompanying sharp drop in viscosity. The suspension gave rise to a clear solution. By adding water, the solution was adjusted to an active content of 35% by weight. The rhamnolipid purity was >90% by weight, based on the dry mass. For the synthesis the rhamnolipid was freeze-dried.

Rhamnolipid species verified by HPLC were:

| RL total [%] (HPLC) | 91 |
|---|---|
| diRL-C8C10 | 13.9 |
| monoRL-C8C10 | 0.51 |
| diRL-C10C10 | 61.4 |
| monoRL -C10C10 | 1.4 |
| diRL-C10C12:1 | 5.9 |
| diRL-C10C12 | 5.5 |
| other RL | 2.2 |

Example 2: Preparation of Mono-Rhamnolipids

The 35% by weight rhamnolipid solution prepared as described above was diluted to 1% by adding water. Two litres of this solution were heated to 50° C. With gentle stirring, 200 units of a thermostable rhamnosidase (ThermoActive™ Rhamnosidase A, Prokazyme) were added and the reaction was carried out overnight. After 20 h, a sample of the solution was analysed by means of HPLC. The di-rhamnolipid had been completely converted to mono-rhamnolipid and rhamnose. Then, the enzyme was deactivated for one hour at 80° C. The entire mixture was freeze-dried.

Example 3: Synthesis of Di-Rhamnolipid-Di-Ester 1

25 g of freeze-dried di-rhamnolipid from example 1 with 6.6 ml of diisopropylcarbodiimide were dissolved in THF and stirred under nitrogen at 55° C. for 1 hour. Next 1.6 grams of 1,4-butanediol and 1% (w/w) of 4-dimethylaminopyridine were added and stirring was continued at 55° C. for 20 h. The reaction was quenched by adding 2 ml of water and the mixture was stirred and slowly cooled to 2° C. and stirring continued for 2 hours. The solids were filtered off over a glass filter. The cake was washed with a mixture of ethanol and water (6:1). Further purification could be achieved by reverse liquid chromatography.

Example 4: Synthesis of Di-Rhamnolipid-Di-Ester 2

A mixture 25 g of freeze-dried di-rhamnolipid from example 1 with 4.4 grams of N-Hydroxy-succinimide (HSU) were dissolved in THF and stirred under nitrogen at RT for 1 hour. 6.6 ml of diisopropylcarbodiimide was added into the mixture over a period of ca 10 minutes, rinsed with 2 ml of THF. The mixture was stirred at 55° C. for 1 hour. Next 2 grams of 1,4-cyclohexanediol were added and stirring was continued at 55° C. for 7 hours and at 50° C. overnight. The next day 2 ml of water were added to quench the reaction. The mixture was distilled half off and additional 50 ml methanol were added and the mixture was stirred at 50° C. The turbid mixture was slowly cooled to 2° C. and stirred for 5 hours. The solids were filtered off over a glass filter. The cake was washed with a mixture of ethanol and water (6:1). Further purification could be achieved by reverse liquid chromatography.

Example 5: Synthesis of Mono-Rhamnolipid-Di-Ester 1

25 g of freeze-dried mono-rhamnolipid from example 2 with 6.9 ml of diisopropylcarbodiimide were dissolved in THF and stirred under nitrogen at 55° C. for 1 hour. Next 2.6 grams of 1,6-hexanediol and 1% (w/w) of 4-dimethylaminopyridine were added and stirring was continued at 55° C. for 20 h. The reaction was quenched by adding 2 ml of water and the mixture was slowly cooled to 2° C. under stirring and continued for 2 hours. The solids were filtered off over a glass filter. The cake was washed with a mixture of ethanol and water (6:1). Further purification could be achieved by reverse liquid chromatography.

Example 6: Synthesis of Mono-Rhamnolipid-Di-Ester 2

A mixture 25 g of freeze-dried mono-rhamnolipid from example 2 with 5.7 grams of N-Hydroxy-succinimide (HSU) were dissolved in THF and stirred under nitrogen at RT for 1 hour. 8.5 ml of diisopropylcarbodiimide were added to the mixture over a period of ca 10 minutes, rinsed with 2 ml of THF. The mixture was stirred at 55° C. for 1 hour. Next 3.2 grams of 1,4-cyclohexanedimethan were added and stirring was continued at 55° C. for 7 hours and at 50° C. overnight. The next day 2 ml of water were added to quench the reaction. The mixture was distilled half off and additional 50 ml methanol were added and the mixture was stirred at 50° C. The turbid mixture was slowly cooled to 2° C. and stirred for 5 hours. The solids were filtered off over a glass filter. The cake was washed with a mixture of ethanol and water (6:1). Further purification could be achieved by reverse liquid chromatography.

Example 7: Synthesis of Mixed Mono/Di-Rhamnolipid-Di-Ester

A mixture 20 g of freeze-dried di-rhamnolipid from example 1, 15 g of mono-rhamnolipid from example 2 and 11 ml of diisopropylcarbodiimide were dissolved in THF and stirred under nitrogen at 55° C. for 1 hour. Next 2.5 grams of 1,4-Butanediol and 1% (w/w) of 4-dimethylaminopyridine were added and stirring was continued at 55° C. for 20 h. The reaction was quenched by adding 4 ml of water and the mixture was stirred and slowly cooled to 2° C. and stirred for 5 hours. The solids were filtered off over a glass filter. The cake was washed with a mixture of ethanol and water (6:1), dried at 40° C. over night under vacuum.

Example 8: Application Effects

In order to measure the influence of the specified structures on producing underarm sweating and odor. The following application tests with the formulations according to the invention were carried out.

The following formulations were prepared 24 hours before use. Typically, 500 g of formulation were prepared in a 800 mL beaker. If ingredients/phases need to be heated, a water bath was used. Mixing was done by a four-blade-stirrer, driven by a Eurostar 20 digital by IKA (IKAWerke, Staufen, Germany) if not otherwise stated.

Example 8.1

500 g of the formulation were prepared as follows: Oils (Phase A) and aqueous phase (Phase B, part of the water, butylene glycol and, if indicated the inventive structures) were mixed separately and heated up under stirring to 80° C. The rest of the water and PEG-6000 Distearate were also mixed separately and heated to 80° C.

Phase B was slowly added to phase A while stirred with a four-blade-stirrer at 250 rpm in a 800 mL beaker within 5 minutes. Then, phase C was added within 1 minute, the mixture is still mixed and kept at 80° C. during the process. After addition of phase C, the mixture was stirred well (1000 rpm, 3 minutes), and then allowed to cool down to 40° C. with gentle stirring (100 rpm). Phase D was added at 40° C. under well stirring (1000 rpm, 3 minutes), phase E was then added under stirring (1 minute, 250 rpm). The whole mixture then needs to cool down to room temperature under well stirring (1000 rpm).

| Phase | | 8.1.1 | 8.1.2 | 8.1.3 | 8.1.4 | 8.1.5 | 8.1.6 | 8.1.7 |
|---|---|---|---|---|---|---|---|---|
| A | Isoceteth-20 | 5 | 5 | 5 | 5 | 5 | 5 | 5 |
| | Diethylhexyl Carbonate | 3 | 3 | 3 | 3 | 3 | 3 | 3 |
| | Triisostearin | 2 | 2 | 2 | 2 | 2 | 2 | 2 |
| | Glyceryl Isostearate | 2.5 | 2.5 | 2.5 | 2.5 | 2.5 | 2.5 | 2.5 |
| B | Water | 52.5 | 52.5 | 52.5 | 52.5 | 52.5 | 52.5 | 52.5 |
| | Butylene Gylcol | 3 | 3 | 3 | 3 | 3 | 3 | 3 |
| C | Water | 9 | 19 | 18.5 | 18.5 | 18.5 | 18.5 | 18.5 |
| | PEG-6000 Distearate | 1 | 1 | 1 | 1 | 1 | 1 | 1 |
| D | PEG-18 Glyceryl Oleate/Cocoate | 2 | 2 | 2 | 2 | 2 | 2 | 2 |
| E | Chlorohydrol (Alumminium Cholrohydrate) | 20 | 10 | 10 | 10 | 10 | 10 | 10 |
| B | Example 3 | | | 0.5 | | | | |
| | Example 4 | | | | 0.5 | | | |
| | Example 5 | | | | | 0.5 | | |
| | Example 6 | | | | | | 0.5 | |
| | Example 7 | | | | | | | 0.5 |
| | | Roll-on | Roll-on | Roll-on | Roll-on | Roll-on | Roll-on | Roll-on |

Formulations 8.1.3 to 8.1.7 are formulations according to the instant invention

Example 8.2

The following formulations were prepared:

Water (phase A) was heated to 75° C. to dissolve the Xanthan Gum (phase B) while stirring (at least 15 minutes, 1000 rpm). The mixture was then cooled to room temperature (100 rpm) to add the ethanol (Phase C). Then, all other ingredients (Phase D) can be added under slight mixing (100 rpm-250 rpm).

| Phase | | 8.2.1 | 8.2.2 | 8.2.3 | 8.2.4 | 8.2.5 | 8.2.6 | 8.2.7 |
|---|---|---|---|---|---|---|---|---|
| A | Water | 77.8 | 77.3 | 77.3 | 77.3 | 77.3 | 77.3 | 77.3 |
| B | Xanthan Gum | 0.4 | 0.4 | 0.4 | 0.4 | 0.4 | 0.4 | 0.4 |
| C | Ethylalcohol | 20.0 | 20.0 | 20.0 | 20.0 | 20.0 | 20.0 | 20.0 |
| D | Propylen Glycol | 1 | 1 | 1 | 1 | 1 | 1 | 1 |
| | Ethylhexylglycerin | 0.3 | 0.3 | 0.3 | 0.3 | 0.3 | 0.3 | 0.3 |

-continued

| Phase | | 8.2.1 | 8.2.2 | 8.2.3 | 8.2.4 | 8.2.5 | 8.2.6 | 8.2.7 |
|---|---|---|---|---|---|---|---|---|
| | Citric acid to pH 5.5 | q.s. | q.s. | q.s. | q.s. | q.s. | q.s. | q.s. |
| | Panthenol | 0.5 | 0.5 | 0.5 | 0.5 | 0.5 | 0.5 | 0.5 |
| A | Example 2 | | 0.5 | | | | | |
| | Example 3 | | | 0.5 | | | | |
| | Example 4 | | | | 0.5 | | | |
| | Example 5 | | | | | 0.5 | | |
| | Example 6 | | | | | | 0.5 | |
| | Example 7 | | | | | | | 0.5 |
| | | spray | spray | spray | Spray | spray | Spray | spray |

Formulations 8.2.2 to 8.2.7 are formulations according to the instant invention

Example 8.3

This deo-stick formulation was prepared 48 hours before application to allow the formulation to solidify completely.

Glycol, glycerine and water (Phase A) were heated to 60° C. and the sodium hydroxide was added (phase B). This mixture was then heated under stirring (100 rpm) to 90° C. and the fatty acids are added (phase C). The mixture was mixed at 90° C. until it appears homogeneously (typically 60 minutes, 100 rpm). The pH of the formulation was checked (dilution of a small part of the formulation with water), pH-value should be between pH 8 and pH 9. The hot mixture was then filled into deo stick tubes and allowed to solidify at room temperature within 24 hours to give light yellowish pasty sticks.

| Phase | | 8.3.1 | 8.3.2 | 8.3.3 | 8.3.4 | 8.3.5 | 8.3.6 | 8.3.7 |
|---|---|---|---|---|---|---|---|---|
| A | Propandiol | 57 | 58 | 57.5 | 57.6 | 57.7 | 57.1 | 57.0 |
| | Glycerin | 22.5 | 22.5 | 22.5 | 22.5 | 22.5 | 22.5 | 22.5 |
| | Water | 2.55 | 2.55 | 2.55 | 2.55 | 2.55 | 2.55 | 2.55 |
| B | Sodium Hydroxide 10% | 9.9 | 9.9 | 9.9 | 9.9 | 9.9 | 9.9 | 9.9 |
| C | Stearic Acid | 3.15 | 3.15 | 3.15 | 3.15 | 3.15 | 3.15 | 3.15 |
| | Palmitic Acid | 3.15 | 3.15 | 3.15 | 3.15 | 3.15 | 3.15 | 3.15 |
| | Ethylhexylglycerin | 0.75 | 0.75 | 0.75 | 0.75 | 0.75 | 0.75 | 0.75 |
| A | Example 1 | 0.4 | | | | | | |
| | di-rhamnolipid hexylester (monoester) | | 0.4 | | | | | |
| | Example 3 | | | 0.2 | | | | |
| | Example 4 | | | | 0.3 | | | |
| | Example 5 | | | | | 0.4 | | |
| | Example 6 | | | | | | 0.8 | |
| | Example 7 | | | | | | | 0.9 |
| | | Deo-stick | Deo-stick | Deo-stick | Deo-stick | Deo-stick | Deo-stick | Deo-stick |

Formulations 8.3.3 to 8.3.7 are formulations according to the instant invention di-Rhamnolipid hexylester was prepared as described in example 3 of WO2017144317; instead of lauryl-alcohol, n-hexyl alcohol was used at equal molar amount.

Example 8.4

After phases A and B were prepared separately at room temperature, phase A was added to phase B under stirring (300 rpm, 1 minute). The mixture was then homogenized (5 minutes, 1800 rpm) to obtain a lotion. Then the polymers were added (Phase C) under stirring, followed by a short homogenization step (0.5 minutes, 300 rpm, 1 minute 1800 rpm). Finally, the sodium hydroxide was added (phase D) under stirring (10 minutes, 500 rpm) to obtain a lotion.

| Phase | | 8.4.1 | 8.4.2 | 8.4.3 | 8.4.4 | 8.4.5 | 8.4.6 | 8.4.7 |
|---|---|---|---|---|---|---|---|---|
| A | Abil Care 85 | 2 | 2 | 2 | 2 | 2 | 2 | 2 |
| | Cyclopentasiloxane | 8 | 8 | 8 | 8 | 8 | 8 | 8 |
| B | Polysorbate 80 | 0.2 | 0.2 | 0.2 | 0.2 | 0.2 | 0.2 | 0.2 |
| | Water | 83.67 | 79.67 | 80.82 | 81.57 | 84.32 | 84.47 | 83.97 |
| | Allantoin | 0.1 | 0.1 | 0.1 | 0.1 | 0.1 | 0.1 | 0.1 |
| | Propylene Glycol | 2 | 2 | 2 | 2 | 2 | 2 | 2 |
| C | Carbomer | 0.2 | 0.2 | 0.2 | 0.2 | 0.2 | 0.2 | 0.2 |
| | Xanthan Gum | 0.07 | 0.07 | 0.07 | 0.07 | 0.07 | 0.07 | 0.07 |
| | Mineral Oil (30 mPas) | 1.06 | 1.06 | 1.06 | 1.06 | 1.06 | 1.06 | 1.06 |
| D | Sodium Hydroxide (10%) | 0.7 | 0.7 | 0.7 | 0.7 | 0.7 | 0.7 | 0.7 |
| B | Example 1 | 1 | 5 | | | | | |
| | Phenoxyethanol, Caprylyl Glycol | 1 | 1 | 1 | 1 | 1 | 1 | 1 |

-continued

| Phase | 8.4.1 | 8.4.2 | 8.4.3 | 8.4.4 | 8.4.5 | 8.4.6 | 8.4.7 |
|---|---|---|---|---|---|---|---|
| Example 3 | | | 3.5 | | | | |
| Example 4 | | | | 2.9 | | | |
| Example 5 | | | | | 0.35 | | |
| Example 6 | | | | | | 0.2 | |
| Example 7 | | | | | | | 0.7 |
| | Roll-on | Roll-on | Roll-on | Roll-on | Roll-on | Roll-on | Roll-on |

Formulations 8.4.3 to 8.4.7 are formulations according to the instant invention

Example 8.5

The oil phase (phase A) and the aqueous phase (phase B) were mixed separately and homogenized by a spatula while being heated up to 75° C. Then, phase A was added to phase B while stirring (2 minutes, 500 rpm) followed by a homogenization step (3 minutes, 1800 rpm). After obtaining a milky lotion, the mixture was cooled down while being stirred at 250 rpm.

| Phase | | 8.5.1 | 8.5.2 | 8.5.3 | 8.5.4 | 8.5.5 | 8.5.6 | 8.5.7 |
|---|---|---|---|---|---|---|---|---|
| A | Tego Care APD 18 MB | 5 | 5 | 5 | 5 | 5 | 5 | 5 |
| | Isopropyl Palmitate | 5 | 5 | 5 | 5 | 5 | 5 | 5 |
| B | Water | 85 | 85 | 85 | 85 | 85 | 85 | 85 |
| | Glycerin | 3 | 3 | 3 | 3 | 3 | 3 | 3 |
| | Phenoxyethanol, Caprylyl Glycol | 1 | 1 | 1 | 1 | 1 | 1 | 1 |
| | di-RL-C2-Ester | 1 | | | | | | |
| | m-RL-C8-Ester | | 1 | | | | | |
| | Example 3 | | | 1 | | | | |
| | Example 4 | | | | 1 | | | |
| | Example 5 | | | | | 1 | | |
| | Example 6 | | | | | | 1 | |
| | Example 7 | | | | | | | 1 |
| | | Roll-on not possible, viscosity too high | Roll-on | Roll-on | Roll-on | Roll-on | Roll-on | Roll-on |

Formulations 8.5.3 to 8.5.7 are formulations according to the instant invention di-rhamnolipid ethylester was prepared as described in example 4 of WO2017144317.

di-rhamnolipid octylester was prepared as described in example 3 of WO2017144317; instead of lauryl-alcohol, n-octyl alcohol was used at equal molar amount.

Example 8.6

Formulating this water-in-oil emulsion requires the help of a ultra-turrax® (T 18 digital ultra-turrax, Ika, Ika Werke, Staufen, Germany).

The liquid components of phase A were mixed with a spatula. Then first the zinc stearate was incorporated into the oil phase by the ultra turrax (3 minutes, 10.000 rpm) before the Aerosil was added in similar way (3 minutes, 10.000 rpm). The aqueous phase (phase B) was also mixed with a spatula at room temperature and then slowly added in phase A with minimum input of mixing (2 minutes, 3000 rpm). After complete addition of phase B, the white emulsion was homogenized for short time (1 minute, 10.000 rpm) and filled into applicators.

| Phase | | 8.6.1 | 8.6.2 | 8.6.3 | 8.6.4 | 8.6.5 | 8.6.6 | 8.6.7 |
|---|---|---|---|---|---|---|---|---|
| A | Abil EM 97 S | 1.5 | 1.5 | 1.5 | 1.5 | 1.5 | 1.5 | 1.5 |
| | Abil EM 90 | 1.5 | 1.5 | 1.5 | 1.5 | 1.5 | 1.5 | 1.5 |
| | Diethylhexyl Carbonate | 10.9 | 10.9 | 10.9 | 10.9 | 10.9 | 10.9 | 10.9 |
| | Dimethicone 5 mPas | 10.9 | 10.9 | 10.9 | 10.9 | 10.9 | 10.9 | 10.9 |
| | Silica (Aerosil R 812) | 0.3 | 0.3 | 0.3 | 0.3 | 0.3 | 0.3 | 0.3 |
| | Zinc stearate | 0.5 | 0.5 | 0.5 | 0.5 | 0.5 | 0.5 | 0.5 |
| B | Water | 65 | 65 | 65 | 65 | 65 | 65 | 65 |
| | Glycerin | 3 | 3 | 3 | 3 | 3 | 3 | 3 |
| | Sodium Chloride | 0.7 | 0.7 | 0.7 | 0.7 | 0.7 | 0.7 | 0.7 |
| | Phenoxyethanol, Caprylyl Glycol | 0.7 | 0.7 | 0.7 | 0.7 | 0.7 | 0.7 | 0.7 |
| | di-RL C2 Ester | 5 | | | | | | |

-continued

| Phase | 8.6.1 | 8.6.2 | 8.6.3 | 8.6.4 | 8.6.5 | 8.6.6 | 8.6.7 |
|---|---|---|---|---|---|---|---|
| di-RL C18 Ester | | 5 | | | | | |
| Example 3 | | | 5 | | | | |
| Example 4 | | | | 5 | | | |
| Example 5 | | | | | 5 | | |
| Example 6 | | | | | | 5 | |
| Example 7 | | | | | | | 5 |
| | Roll-on | Roll-on | Roll-on | Roll-on | Roll-on not possible, viscosity too high | Roll-on | Roll-on |

Formulations 8.6.3 to 8.6.7 are formulations according to the instant invention
di-Rhamnolipid ethylester was prepared as described in example 4 of WO2017144317.
di-Rhamnolipid octadecylylester was prepared as described in example 3 of WO2017144317; instead of lauryl-alcohol, n-octadecyl alcohol was used at equal molar amount.

Example 9: Panel Testing

Eight panelists were selected for odor tests (panelists are coded with letters A-H). Every panelist was equipped with a wash lotion as described in table 1.

TABLE 1

| perfume free wash lotion for cleaning of underarms of panelists | | | |
|---|---|---|---|
| INCI | Tradename/Supplier | Active matter/ % | Concentration/ % |
| water | | | 13.7 |
| PEG-7 Glyceryl Cocoate | TEGOSOFT ® GC/Evonik | 100 | 5.4 |
| Sodium Laureth Sulfate | Texapon NSO/BASF | 28 | 65.80 |
| Cocamidopropyl Betaine; Glyceryl Laurate | TEGO ® Betain HS/Evonik | | 10.00 |
| PEG-18 Glyceryl Oleate/Cocoate | ANTIL ® 171/Evonik | 100 | 4.10 |
| Verstatil PC | Phenoxyethanol, Caprylyl Glycol/ Evonik | 100 | 1 |

This wash lotion was free of perfumes to avoid an influence of artificial odors on the panel results.

The panelists were asked to clean their armpits as usual in their daily routine, however, the panelists used the perfume free wash lotion provided. After cleaning, the formulations described in the section above were applied. The formulations were packed in neutral containers which were randomly labeled. Thus, the inventive formulations were applied also randomly under the left or the right arm. The panelists were also advised to use no additional perfume. The panelists applied the formulations in the morning and the degree of malodor was accessed after 8-10 hours after application. The panelists followed the normal working routine, the artificial sweat generation in hot rooms was not used since the formulations were evaluated in pairwise discrimination.

Six trained examiners evaluated the malodor intensity scale of the panelists after 8-10 hours. The ratings were given according to the malodor intensity scale ranging from 0 to 10. (see IFSCC Monograph, Number 6, "Antiperspirants and Deodorants: Priciples of Underarm Technology" Copyright© International Federation of the Societies of Cosmetic Chemists 1998; ISBN 1-870228-19-7 and Table 2).

The examiners scored the odor of the armpits of the panelists, the difference of the evaluation were calculated per examiner to visualize the pairwise difference perceived by the examiner. After all six examiners gave their evaluation on one panelists, the difference of the pairwise evaluation is averaged. A difference of the average of 1 is likely to be experienced by an untrained person, whereas a difference of 2 or more is clearly recognized.

TABLE 2

| malodor intensity scale used for description of odor by the examiners | |
|---|---|
| Score | malodor intensity scale |
| 0 | None, no odor |
| 1 | Threshold odor |
| 2 | Very slight odor |
| 3 | Slight odor |
| 4 | Slight to moderate odor |
| 5 | Moderate odor |
| 6 | Slightly strong odor |
| 7 | Moderately strong odor |
| 8 | Strong odor |
| 9 | Very strong odor |
| 10 | Extremly strong odor |

Example 9.1

In a first experiment, formulations 8.1.1 and 8.1.2 were tested. Both formulations contain no molecules according to the instant invention. The difference in loading of aluminium salts should be investigated in that set.

| | Examiner | 1 | 2 | 3 | 4 | 5 | 6 | | difference 8.1.2 to 8.1.1 |
|---|---|---|---|---|---|---|---|---|---|
| Panelist A | left 8.1.2 | 4 | 5 | 6 | 5 | 6 | 5 | | |
| | right 8.1.1 | 1 | 1 | 1 | 2 | 0 | 0 | | |
| | | −3 | −4 | −5 | −3 | −6 | −5 | −4.33 | 4.33 |
| Panelist B | left 8.1.1 | 2 | 1 | 1 | 2 | 1 | 1 | | |
| | right 8.1.2 | 6 | 5 | 6 | 6 | 6 | 5 | | |
| | | 4 | 4 | 5 | 4 | 5 | 4 | 4.33 | 4.33 |
| Panelist C | left 8.1.2 | 4 | 4 | 5 | 5 | 4 | 5 | | |
| | right 8.1.1 | 2 | 2 | 2 | 1 | 1 | 2 | | |
| | | −2 | −2 | −3 | −4 | −3 | −3 | −2.83 | 2.83 |
| Panelist D | left 8.1.1 | 6 | 4 | 4 | 4 | 5 | 5 | | |
| | right 8.1.2 | 10 | 7 | 8 | 8 | 9 | 8 | | |
| | | 4 | 3 | 4 | 4 | 4 | 3 | 3.67 | 3.67 |
| Panelist E | left 8.1.2 | 8 | 6 | 7 | 6 | 7 | 7 | | |
| | right 8.1.1 | 3 | 2 | 4 | 2 | 3 | 3 | | |
| | | −5 | −4 | −3 | −4 | −4 | −4 | −4.00 | 4.00 |
| Panelist F | left 8.1.1 | 2 | 2 | 2 | 3 | 2 | 1 | | |
| | right 8.1.2 | 5 | 5 | 6 | 7 | 6 | 6 | | |
| | | 3 | 3 | 4 | 4 | 4 | 5 | 3.83 | 3.83 |
| Panelist G | left 8.1.2 | 5 | 6 | 4 | 5 | 6 | 6 | | |
| | right 8.1.1 | 1 | 1 | 2 | 1 | 1 | 2 | | |
| | | −4 | −5 | −2 | −4 | −5 | −4 | −4.00 | 4.00 |
| Panelist H | left 8.1.2 | 6 | 6 | 6 | 5 | 5 | 6 | | |
| | right 8.1.1 | 3 | 2 | 2 | 3 | 2 | 2 | | |
| | | −3 | −4 | −4 | −2 | −3 | −4 | −3.33 | 3.33 |
| Average of differences over all panellists | | | | | | | | | 3.79 |

Results: It is obvious that the formulation with 20% aluminium salt (8.1.1) outperformed the formulation with 10% salt (8.1.2).

Example 9.2

The next set of experiments was made in order to see if the inventive structures can compensate the lower level of aluminium salt. Thus formulation 8.1.1 (20% aluminium salt) was tested against formulation 8.1.4 (10% aluminium salt+inventive structure 4)

| | Examiner | 1 | 2 | 3 | 4 | 5 | 6 | | difference 8.1.1 to 8.1.4 |
|---|---|---|---|---|---|---|---|---|---|
| Panelist A | left 8.1.1 | 2 | 3 | 1 | 2 | 3 | 2 | | |
| | **right** 8.1.4 | 2 | 1 | 2 | 1 | 2 | 3 | | |
| | | 0 | −2 | 1 | −1 | −1 | 1 | −0.33 | 0.33 |
| Panelist B | **left** 8.1.4 | 1 | 1 | 2 | 2 | 1 | 3 | | |
| | right 8.1.1 | 0 | 2 | 3 | 1 | 2 | 2 | | |
| | | −1 | 1 | 1 | −1 | 1 | −1 | 0.00 | 0.00 |
| Panelist C | **left** 8.1.4 | 1 | 2 | 3 | 2 | 3 | 2 | | |
| | right 8.1.1 | 3 | 1 | 1 | 3 | 1 | 3 | | |
| | | 2 | −1 | −2 | 1 | −2 | 1 | −0.17 | −0.17 |
| Panelist D | **left** 8.1.4 | 5 | 5 | 6 | 7 | 7 | 8 | | |
| | right 8.1.1 | 6 | 6 | 6 | 5 | 7 | 7 | | |
| | | 1 | 1 | 0 | −2 | 0 | −1 | −0.17 | −0.17 |
| Panelist E | **left** 8.1.4 | 6 | 6 | 5 | 8 | 5 | 7 | | |
| | right 8.1.1 | 7 | 5 | 4 | 6 | 7 | 6 | | |
| | | 1 | −1 | −1 | −2 | 2 | −1 | −0.33 | −0.33 |
| Panelist F | left 8.1.1 | 2 | 2 | 2 | 3 | 2 | 2 | | |
| | **right** 8.1.4 | 1 | 3 | 2 | 2 | 1 | 2 | | |
| | | −1 | 1 | 0 | −1 | −1 | 0 | −0.33 | 0.33 |
| Panelist G | left 8.1.1 | 1 | 2 | 2 | 1 | 0 | 2 | | |
| | **right** 8.1.4 | 0 | 3 | 1 | 0 | 2 | 1 | | |
| | | −1 | 1 | −1 | −1 | 2 | −1 | −0.17 | 0.17 |
| Panelist H | **left** 8.1.4 | 0 | 1 | 2 | 2 | 2 | 1 | | |
| | right 8.1.1 | 1 | 2 | 1 | 1 | 2 | 0 | | |
| | | 1 | 1 | −1 | −1 | 0 | −1 | −0.17 | −0.17 |
| Average of differences over all panellists | | | | | | | | | 0.00 |

Results: The two formulations could not be differentiated by the examiners, inventive structure 4 is able to compensate the reduced amount of aluminium salt.

Example 9.3

8.2.2 vs. 8.2.7

| | Examiner | 1 | 2 | 3 | 4 | 5 | 6 | | difference 8.2.7 to 8.2.2 |
|---|---|---|---|---|---|---|---|---|---|
| Panelist A | **left** 8.2.7 | 2 | 2 | 1 | 2 | 2 | 2 | | |
| | right 8.2.2 | 3 | 4 | 3 | 5 | 3 | 2 | | |
| | | 1 | 2 | 2 | 3 | 1 | 0 | 1.50 | 1.50 |
| Panelist B | **left** 8.2.7 | 5 | 4 | 2 | 3 | 3 | 4 | | |
| | right 8.2.2 | 7 | 7 | 6 | 5 | 4 | 7 | | |
| | | 2 | 3 | 4 | 2 | 1 | 3 | 2.50 | 2.50 |
| Panelist C | left 8.2.2 | 5 | 3 | 2 | 4 | 5 | 6 | | |
| | **right** 8.2.7 | 3 | 2 | 2 | 2 | 3 | 3 | | |
| | | −2 | −1 | 0 | −2 | −2 | −3 | −1.67 | 1.67 |
| Panelist D | **left** 8.2.7 | 6 | 5 | 4 | 5 | 5 | 6 | | |
| | right 8.2.2 | 8 | 7 | 8 | 8 | 9 | 9 | | |
| | | 2 | 2 | 4 | 3 | 4 | 3 | 3.00 | 3.00 |
| Panelist E | **left** 8.2.7 | 5 | 5 | 5 | 4 | 7 | 6 | | |
| | right 8.2.2 | 8 | 9 | 7 | 8 | 10 | 9 | | |
| | | 3 | 4 | 2 | 4 | 3 | 3 | 3.17 | 3.17 |
| Panelist F | left 8.2.2 | 5 | 4 | 4 | 4 | 3 | 4 | | |
| | **right** 8.2.7 | 2 | 2 | 1 | 2 | 2 | 3 | | |
| | | −3 | −2 | −3 | −2 | −1 | −1 | −2.00 | 2.00 |
| Panelist G | left 8.2.2 | 4 | 4 | 5 | 3 | 3 | 3 | | |
| | **right** 8.2.7 | 2 | 2 | 2 | 2 | 1 | 2 | | |
| | | −2 | −2 | −3 | −1 | −2 | −1 | −1.83 | 1.83 |
| Panelist H | left 8.2.2 | 3 | 4 | 4 | 3 | 3 | 2 | | |
| | **right** 8.2.7 | 2 | 3 | 3 | 2 | 1 | 2 | | |
| | | −1 | −1 | −1 | −1 | −2 | 0 | −1.00 | 1.00 |
| Average of differences over all panellists | | | | | | | | | 2.08 |

Results: The results clearly show that the inventive structure 7 is able to reduce malodor.

Example 9.4

| | Examiner | 1 | 2 | 3 | 4 | 5 | 6 | | difference 8.3.1 to 8.3.3 |
|---|---|---|---|---|---|---|---|---|---|
| Panelist A | left 8.3.1 | 3 | 4 | 5 | 3 | 3 | 4 | | |
| | **right** 8.3.3 | 1 | 2 | 1 | 0 | 1 | 2 | | |
| | | 2 | 2 | 4 | 3 | 2 | 2 | 2.50 | 2.50 |
| Panelist B | left 8.3.1 | 5 | 3 | 3 | 4 | 2 | 3 | | |
| | **right** 8.3.3 | 1 | 0 | 2 | 1 | 1 | 1 | | |
| | | −4 | −3 | −1 | −3 | −1 | −2 | −2.33 | 2.33 |
| Panelist C | **left** 8.3.3 | 2 | 2 | 4 | 3 | 4 | 1 | | |
| | right 8.3.1 | 4 | 6 | 6 | 6 | 7 | 5 | | |
| | | 2 | 4 | 2 | 3 | 3 | 4 | 3.00 | 3.00 |
| Panelist D | left 8.3.1 | 8 | 7 | 10 | 9 | 9 | 8 | | |
| | **right** 8.3.3 | 4 | 5 | 7 | 4 | 5 | 6 | | |
| | | 4 | 2 | 3 | 5 | 4 | 2 | 3.33 | 3.33 |
| Panelist E | **left** 8.3.3 | 2 | 3 | 5 | 4 | 3 | 2 | | |
| | right 8.3.1 | 7 | 8 | 8 | 9 | 9 | 9 | | |
| | | 5 | 5 | 3 | 5 | 6 | 7 | 5.17 | 5.17 |
| Panelist F | **left** 8.3.3 | 2 | 3 | 4 | 3 | 2 | 1 | | |
| | right 8.3.1 | 6 | 7 | 5 | 5 | 4 | 4 | | |
| | | −4 | −4 | −1 | −2 | −2 | −3 | −2.67 | 2.67 |
| Panelist G | left 8.3.1 | 6 | 5 | 5 | 5 | 7 | 4 | | |
| | **right** 8.3.3 | 3 | 2 | 3 | 3 | 4 | 1 | | |
| | | −3 | −3 | −2 | −2 | −3 | −3 | −2.67 | 2.67 |
| Panelist H | **left** 8.3.3 | 1 | 1 | 3 | 1 | 2 | 2 | | |
| | right 8.3.1 | 5 | 6 | 4 | 3 | 3 | 4 | | |
| | | 4 | 5 | 1 | 2 | 1 | 2 | 2.50 | 2.50 |
| Average of differences over all panellists | | | | | | | | | 3.02 |

Results: The inventive structure 3 is superior in reduction of malodors as compared to the pure di-Rhamnolipid.

Example 9.5

8.3.2 vs 8.3.5

| | Examiner | 1 | 2 | 3 | 4 | 5 | 6 | | difference 8.3.5 to 8.3.2 |
|---|---|---|---|---|---|---|---|---|---|
| Panelist A | **left** 8.3.5 | 1 | 1 | 0 | 1 | 2 | 1 | | |
| | right 8.3.2 | 2 | 3 | 3 | 4 | 4 | 4 | | |
| | | 1 | 2 | 3 | 3 | 2 | 3 | 2.33 | 2.33 |
| Panelist B | left 8.3.2 | 3 | 3 | 4 | 4 | 3 | 3 | | |
| | **right** 8.3.5 | 1 | 1 | 1 | 2 | 2 | 1 | | |
| | | −2 | −2 | −3 | −2 | −1 | −2 | −2.00 | 2.00 |
| Panelist C | **left** 8.3.5 | 3 | 3 | 2 | 3 | 4 | 2 | | |
| | right 8.3.2 | 5 | 6 | 5 | 6 | 6 | 4 | | |
| | | 2 | 3 | 3 | 3 | 2 | 2 | 2.50 | 2.50 |
| Panelist D | **left** 8.3.5 | 5 | 5 | 6 | 5 | 6 | 7 | | |
| | right 8.3.2 | 8 | 8 | 10 | 9 | 9 | 9 | | |
| | | 3 | 3 | 4 | 4 | 3 | 2 | 3.17 | 3.17 |
| Panelist E | **left** 8.3.5 | 4 | 5 | 5 | 5 | 5 | 4 | | |
| | right 8.3.2 | 8 | 8 | 9 | 10 | 9 | 10 | | |
| | | 4 | 3 | 4 | 5 | 4 | 6 | 4.33 | 4.33 |
| Panelist F | left 8.3.2 | 5 | 6 | 6 | 5 | 4 | 5 | | |
| | **right** 8.3.5 | 3 | 2 | 2 | 3 | 2 | 2 | | |
| | | −2 | −4 | −4 | −2 | −2 | −3 | −2.83 | 2.83 |
| Panelist G | left 8.3.2 | 5 | 5 | 6 | 5 | 6 | 4 | | |
| | **right** 8.3.5 | 2 | 2 | 3 | 3 | 2 | 1 | | |
| | | −3 | −3 | −3 | −2 | −4 | −3 | −3.00 | 3.00 |
| Panelist H | **left** 8.3.5 | 2 | 2 | 2 | 1 | 2 | 3 | | |
| | right 8.3.2 | 4 | 5 | 4 | 3 | 4 | 6 | | |
| | | 2 | 3 | 2 | 2 | 2 | 3 | 2.33 | 2.33 |
| Average of differences over all panellists | | | | | | | | | 2.81 |

Results: The incentive structure 5 is superior in reduction of malodors as compared to the pure di-Rhamnolipid Hexylester. Furthermore, Panelists A, C, D, G and H complained on itching skin in the armpits treated with formulation 8.3.2.

Example 9.6

| | Examiner | 1 | 2 | 3 | 4 | 5 | 6 | | difference 8.5.2 to 8.5.6 |
|---|---|---|---|---|---|---|---|---|---|
| Panelist A | left 8.5.2 | 8 | 7 | 6 | 7 | 8 | 8 | | |
| | **right** 8.5.6 | 3 | 4 | 2 | 4 | 5 | 5 | | |
| | | −5 | −3 | −4 | −3 | −3 | −3 | −3.50 | 3.50 |
| Panelist B | **left** 8.5.6 | 7 | 7 | 6 | 8 | 7 | 6 | | |
| | right 8.5.2 | 4 | 4 | 3 | 5 | 4 | 4 | | |
| | | −3 | −3 | −3 | −3 | −3 | −2 | −2.83 | 2.83 |
| Panelist C | **left** 8.5.6 | 3 | 3 | 4 | 4 | 4 | 3 | | |
| | right 8.5.2 | 8 | 8 | 7 | 6 | 7 | 7 | | |
| | | 5 | 5 | 3 | 2 | 3 | 4 | 3.67 | 3.67 |
| Panelist D | left 8.5.2 | 10 | 10 | 8 | 9 | 9 | 9 | | |
| | **right** 8.5.6 | 5 | 5 | 5 | 5 | 4 | 6 | | |
| | | −5 | −5 | −3 | −4 | −5 | −3 | −4.17 | 4.17 |
| Panelist E | **left** 8.5.6 | 5 | 5 | 4 | 7 | 5 | 6 | | |
| | right 8.5.2 | 9 | 8 | 10 | 10 | 8 | 8 | | |
| | | 4 | 3 | 6 | 3 | 3 | 2 | 3.50 | 3.50 |
| Panelist F | **left** 8.5.6 | 5 | 7 | 8 | 7 | 7 | 8 | | |
| | right 8.5.2 | 5 | 4 | 6 | 5 | 5 | 5 | | |
| | | 0 | −3 | −2 | −2 | −2 | −3 | −2.00 | 2.00 |
| Panelist G | left 8.5.2 | 6 | 6 | 7 | 8 | 6 | 6 | | |
| | **right** 8.5.6 | 3 | 2 | 5 | 5 | 4 | 2 | | |
| | | −3 | −4 | −2 | −3 | −2 | −4 | −3.00 | 3.00 |
| Panelist H | left 8.5.2 | 8 | 7 | 6 | 8 | 7 | 8 | | |
| | **right** 8.5.6 | 3 | 4 | 5 | 5 | 5 | 4 | | |
| | | −5 | −3 | −1 | −3 | −2 | −4 | −3.00 | 3.00 |
| Average of differences over all panellists | | | | | | | | | 3.21 |

Results: The set of data clearly shows that the inventive oligo ester of mono-rhamnolipid is better suited in reduction of malodor as compared to the mono-ester.

List of Ingredients Used

| INCI | Tradename | Supplier |
|---|---|---|
| Isoceteth-20 | Tego Alkaonol IC 20 | Evonik |
| Diethylhexyl Carbonate | Tegosoft DEC | Evonik |
| Triisostearin | Tegosoft TIS | Evonik |
| Glyceryl Isostearate | Sympatens-GMIS | KLK Oleo Europe |
| Butylene Gylcol | Butylene Gylcol | Dow |
| PEG-6000 Distearate | Rewopal PEG 6000 DS | Evonik |
| PEG-18 Glyceryl Oleate/Cocoate | Antil 171 | Evonik |
| Alumminium Cholrohydrate | Chlorohydrol | Elementis |
| Xanthan Gum | Satiaxane | Cargill |
| Ethylalcohol | Ethanol | Cremer Oleo |
| Propylen Glycol | Propylen Glycol | Dow |
| Ethylhexylglycerin | Ethylhexylglycerin | Hubei Artec Biotechnology Co., Ltd. |
| Citric acid | Citric acid | Sigma Aldrich |
| Panthenol | Panthenol | Parchem |
| Glycerin | Glycerin | Cremer Oleo |
| Sodium Hydroxide 10% | Sodium Hydroxide | Sigma Aldrich |
| Stearic Acid | CremerAC SA 18/92 | Cremer Oleo |
| Palmitic Acid | CremerAC C16/98 | Cremer Oleo |
| Bis-PEG/PPG-16/16 PEG/PPG-16/16 Dimethicone (and) Caprylic/Capric Triglyceride | Abil Care 85 | Evonik |
| Tego SMO 80 V | Polysorbate 80 | Evonik |
| Carbomer | Carbomer 940 | Ashland |
| Mineral Oil | Agrol 13 | Sonneborn |
| Polyglyceryl-6 Stearate (and) Polyglyceryl-6 Behenate (and) C18-22 Hydroxyalkyl Hydroxypropyl Guar | Tego Care APD 18 | Evonik |
| Isopropyl Palmitate | Tegosoft P | Evonik |
| Bis-PEG/PPG-14/14 Dimethicone; Dimethicone | Abil EM 97 S | Evonik |
| Cetyl PEG/PPG-10/1 Dimethicone | Abil EM 90 | Evonik |
| Dimethicone 5 mPas | Belsil DM 5 | Wacker |
| Silica | Aerosil R 812 | Evonik |
| Zinc stearate | Zinc stearate | Sigma Aldrich |
| Sodium Chloride | Sodium Chloride | Sigma Aldrich |
| Phenoxyethanol, Caprylyl Glycol | Verstatil PC | Evonik |
| Phenoxyethanol, Ethylhexylglycerin | Euxyl PE 9010 | Schülke & Mayr |

The invention claimed is:

1. A rhamnolipid (RL) ester of the general formula (I)

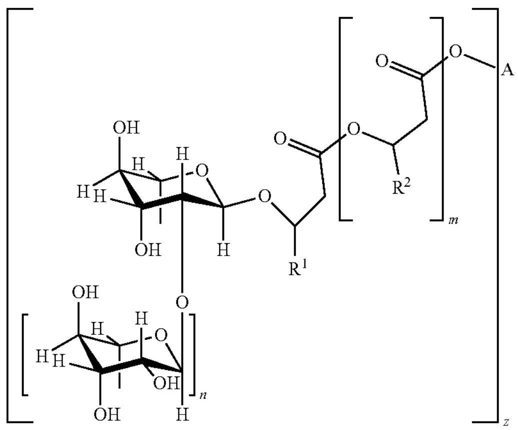

general formula (I), wherein m=independently of one another, identical or different, 2, 1, or 0, n=independently of one another, identical or different, 1 or 0, Z=2 to 10, $R^1$=independently of one another, identical or different, an organic radical having 2 to 24 carbon atoms, $R^2$=independently of one another, identical or different, an organic radical having 2 to 24 carbon atoms, and A is a z-valent organic radical.

2. The rhamnolipid ester according to claim 1, wherein a rhamnolipid radical of the general formula (I) is selected from the group consisting of diRL-C10C10, diRL-C8C10, diRL-C10C12, diRL-C10C12:1, and monoRL-C10C10.

3. The rhamnolipid ester according to claim 1, wherein z=2, and

A is a two valent hydrocarbyl radical, which can be substituted by one or more hydroxyl groups.

4. The rhamnolipid ester according to claim 1, wherein z=2, and

A is selected from the group consisting of

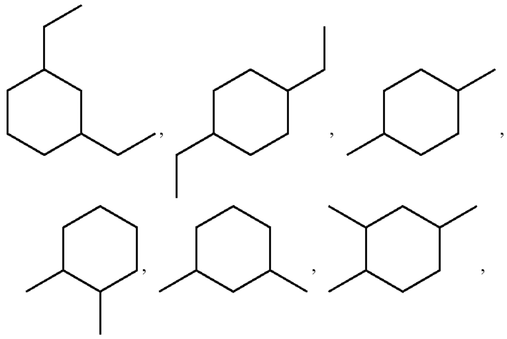

-continued

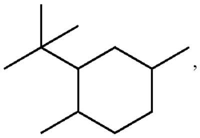, 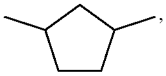,

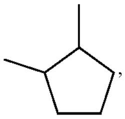, 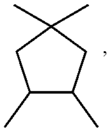, 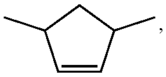,

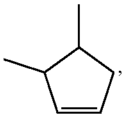,

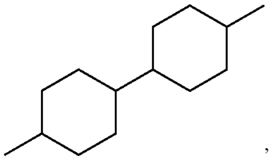, and

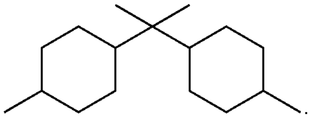.

5. The rhamnolipid ester according to claim 1, wherein z=2, and

A is selected from the group consisting of

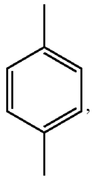, 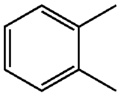, 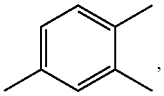,

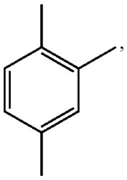, 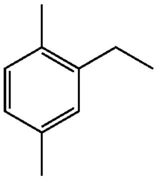, 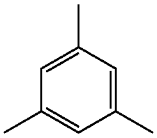,

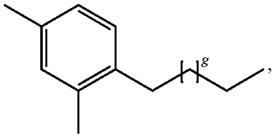, 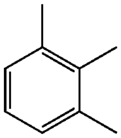, g = 0 bis 10

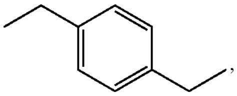, and

-continued

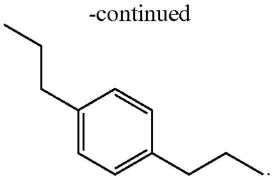.

6. The rhamnolipid ester according to claim 1, wherein a rhamnolipid radical of the general formula (1) is selected from the group consisting of diRL-C10C10, diRL-C8C10, diRL-C10C12, diRL-C10C12:1, and monoRL-C10C10, z=2, and A is selected from the group consisting of

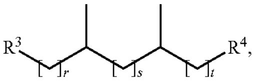, wherein $R^3=R^4=H$, r=t=0, s=0 to 8, 10, 12, or 14,

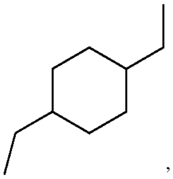, 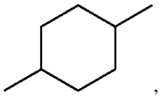,

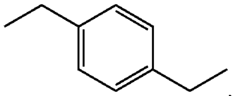, and

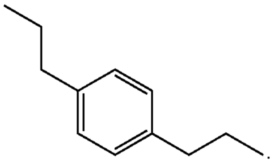.

7. A formulation, comprising at least one rhamnolipid ester according to claim 1.

8. A cosmetic formulation for anti-perspirant applications, comprising:

the rhamnolipid ester according to claim 1.

9. The rhamnolipid ester according to claim 1, wherein in general formula (I), $R^1$=independently of one another, an optionally branched, optionally substituted, and optionally unsaturated alkyl radical; and/or $R^2$=independently of one another, an optionally branched, optionally substituted, and optionally unsaturated alkyl radical.

10. The rhamnolipid ester according to claim 1, wherein in general formula (1), $R^1$=independently of one another, selected from the group consisting of pentenyl, heptenyl, nonenyl, undecenyl, tridecenyl, and $(CH_2)_o—CH_3$ wherein o=1 to 23.

11. The rhamnolipid ester according to claim 1, wherein in general formula (I), $R^2$=independently of one another, selected from the group consisting of pentenyl, heptenyl, nonenyl, undecenyl, tridecenyl, and $(CH_2)_o—CH_3$ wherein o=1 to 23.

12. The rhamnolipid ester according to claim 3, wherein A is

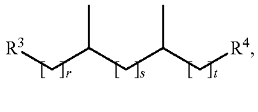

wherein $R^3$ and $R^4$ are $CH_3$ or H, r=0 to 3, s=0 to 24, and t=0 to 24.

13. The rhamnolipid ester according to claim 3, wherein A is

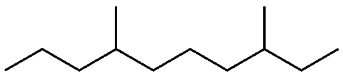

or

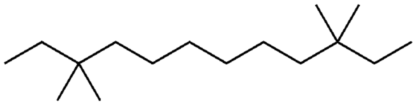

.

14. A process for the preparation of at least one rhamnolipid ester according to claim 1, comprising:

A) providing at least one rhamnolipid,

B) reacting the at least one rhamnolipid with at least one coupling reagent,

C) reacting the at least one rhamnolipid activated by B) with a polyhydric alcohol having 1 to 32 carbon atoms, to obtain the at least one rhamnolipid ester, and optionally, D) purifying the at least one rhamnolipid ester.

15. The process according to claim 14, wherein in B), the at least one coupling reagent is at least one selected from the group consisting of dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl) carbodiimide metho-p-toluenesulphonate, N-benzyl-N'-3' dimethylaminopropylcarbodiimide hydrochloride, 1-ethyl-3-(3-dimethylaminopropyl) carbodiimide, N-ethylcarbodiimide hydrochloride, and carbonyldiimidazole.

16. The process according to claim 14, wherein the reacting in C) is with at least one catalyst selected from the group consisting of N-ethyldiisopropylamine, trialkylamine, pyridine, 4-dimethylaminopyridine, and hydroxybenzotriazole.

17. The process according to claim 14, wherein in A), the at least one rhamnolipid is selected from the group consisting of diRLC10C10, diC8C10, diRLC10C12, diRLC10C12:1, monoRLC10C10, and a mixture thereof.

18. The process according to claim 14, wherein in C), the polyhydric alcohol is at least one selected from the group of 1,2-ethanediol, 1,2-propanediol, 1,3-propanediol, 1,4-butanediol, 1,5-pentanediol, 1,2-hexanediol, 2,5-hexanediol, 1,6-hexanediol, 1,7-heptanediol, 1,8-octandiol, 1,9-nonanediol, 1,10-decanediol, 1,12-dodecanediol, 1,2-dodecanediol, 1,2-tetradecandiol, 1,14-tetradecanediol, and 1,16-hexadecanediol.

19. A method, comprising:

adding the rhamnolipid ester according to claim 1 to a formulation for inhibiting body odor and/or sweat.

* * * * *